United States Patent [19]

Bergman et al.

[11] Patent Number: 4,511,745
[45] Date of Patent: Apr. 16, 1985

[54] PROCESS FOR FUNCTIONALIZING ALKANES

[75] Inventors: Robert G. Bergman, Kensington, Calif.; Andrew H. Janowicz, Wilmington, Del.; Roy A. Periana-Pillai, Berkeley, Calif.

[73] Assignee: The United States of America as represented by the United States Department of Energy, Washington, D.C.

[21] Appl. No.: 619,886

[22] Filed: Jun. 12, 1984

[51] Int. Cl.$^3$ .................... B01J 19/12; C07C 17/00; C07F 15/00
[52] U.S. Cl. .................... 570/241; 570/252; 260/429 CY; 204/162 R
[58] Field of Search ............ 570/1, 241, 252; 260/429 CY; 204/162 R

[56] References Cited

U.S. PATENT DOCUMENTS 3,459,780 8/1969 Wilkinson .................... 570/241
4,138,420 2/1979 Unruh et al. ................ 260/429 CY Primary Examiner—Howard S. Williams
Attorney, Agent, or Firm—Harold M. Dixon; Roger S. Gaither; Judson R. Hightower

[57] ABSTRACT

Process for functionalizing saturated hydrocarbons selectively in the terminal position comprising:
(a) reacting said saturated hydrocarbons of the formula:

RH where:
H represents a hydrogen atom, and
R represents a saturated hydrocarbon radical,
with a metal complex of the formula:

$CpRhPMe_3H_2$ where:
Cp represents a pentamethylated cyclopentadienyl radical,
Rh represents a rhodium atom,
P represents a phosphorous atom,
Me represents a methyl group,
H represents a hydrogen atom,
in the presence of ultraviolet radiation at a temperature maintained at about $-60°$ to $-17°$ C. to form a hydridoalkyl complex of the formula:

$CpRhPMe_3RH$ (b) reacting said hydridoalkyl complex with a haloform of the formula:

$CHX_3$ where:
X represents a bromine, iodine or chlorine atom,
at a temperature in the range of about $-60°$ to $-17°$ C. to form the corresponding haloalkyl complex of step (a) having the formula:

$CpRhPMe_3RX$; and, (c) reacting said haloalkyl complex formed in (b) with halogen ($X_2$) at a temperature in the range of about $-60°$ to $25°$ C. (i.e. ambient) to form a functional haloalkyl compound.

11 Claims, No Drawings

PROCESS FOR FUNCTIONALIZING ALKANES

The invention disclosed herewith arose at the Lawrence Berkeley Laboratory in the course of, or under Contract No. DE-AC03-76SF00098 between the U.S. Department of Energy and the University of California.

FIELD OF THE INVENTION

The present invention relates to functionalizing saturated hydrocarbons, and more particularly relates to functionalizing or enhancing the reactivity of alkanes by converting them to halo-substituted alkanes.

BACKGROUND OF THE INVENTION

Saturated hydrocarbons are obtained from petroleum, natural gas reservoirs, and other petroliferous deposits. They are, on a relative basis to other hydrocarbons, available in a relatively large supply. They have many uses in addition to being suitable as fuels. One of those uses, and one which has a high order of value in terms of uses, is as a raw material in chemical reactions when they can be made to react in an efficient, economical and predictable if not selective fashion. Particularly desirable is the ability to prepare terminally-substituted compounds, because terminally-substituted, or primary functional compounds, are in the greatest demand commercially. However, saturated hydrocarbons have strong C—H and C—C bonds which make the necessary reactions difficult for one or more reasons.

Various approaches to reaction of hydrocarbons have been studied over the years including thermal, chemical and photochemical. Examples of these are set forth in Janowicz and Bergman, J. Am. Chem. Soc. 105, 3929-3939 (1983). Most of these prior methods have consumed large amounts of energy in one form or another; and, importantly have lacked selectivity. Either, in addition to or separately, the prior methods have suffered other disadvantages.

Unsaturated compounds, in addition to being a valuable raw material for reactions which functionalized alkanes are not, do not always form terminally-substituted compounds but form 2-substituted derivatives according to Markovnikoff's rule.

Recently we found that certain organo-iridium complexes are capable of intermolecular oxidative addition to single C—H bonds in saturated hydrocarbons leading to hydridoalkyl iridium complexes which can be used to convert alkanes to alkyl halides. This is reported in Janowicz and Bergman, J.A.C.S. 104, 352 (1982). While this procedure enjoys a degree of benefits over the prior art it leaves room for improvement in several respects. One such important feature in the use of iridium complexes is the need to pass through an organomercurial intermediate. The process using iridium also provides much less selectivity than theoretically possible and desirable.

OBJECTS OF THE INVENTION

It is a principal object of this invention to provide a method of functionalizing saturated hydrocarbons.

It is another object of this invention to provide a method of providing a high degree of selectivity in the functionalizing of alkanes.

It is an important object to provide a method of functionalizing alkanes which can be carried out at relatively mild conditions.

Still another and very important object of this invention is to provide a method which enables starting material to be regenerated and reused.

Yet, another object is to provide a process which does not require the additional step and use of organomercurial intermediates as in the case of iridium centered complexes.

An additional object is to provide a process for functionalizing alkanes which is efficient, relatively economical and has wide application in terms of alkanes which can be treated.

Additional objects, advantages and novel features of the invention will be set forth in part in the description which follows, and in part will become apparent to those skilled in the art upon examination of the following, or will be learned by practice of the invention. The objects and advantages of the invention may be realized and attained by means of the instrumentalities and combinations particularly pointed out in the appended claims.

SUMMARY OF THE INVENTION

A process for functionalizing saturated hydrocarbons comprising:

(a) reacting said saturated hydrocarbons of the formula:

RH where:
H represents a hydrogen atom, and
R represents a saturated hydrocarbon radical,
with a metal complex of the formula:

CpRhPMe$_3$H$_2$ where:
Cp represents a pentamethylated cyclopentadienyl radical,
Rh represents a rhodium atom,
P represents a phosphorous atom,
Me represents a methyl group,
H represents a hydrogen atom, in the presence of ultraviolet radiation at a temperature maintained at about −60° to −17° C. to form a hydridoalkyl complex of the formula:

CpRhPMe$_3$(R)(H)

(b) reacting said hydridoalkyl complex with a haloform of the formula:

CHX$_3$ where:
X represents a halogen atom (i.e., Br, I, or Cl),
at a temperature in the range of about −60° to −17° C. to form the corresponding haloalkyl complex of step (a) having the formula:

CpRhPMe$_3$(R)(X); and, (c) reacting said haloalkyl complex formed in (b) with halogen (X$_2$) at a temperature in the range of about −60° to 25° C. (i.e. ambient) to form a haloalkyl compound and a compound of the formula:
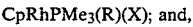

CpRhPMe₃X₂ where:
Cp, Rh, P, Me, and X are the same as above.

In one specific aspect, the process provides a highly selective manner of preparing terminal, primary or 1-substituted halogenated alkyl compounds.

DETAILED DESCRIPTION OF THE INVENTION

In brief, the process can be described illustratively in equation form as follows:

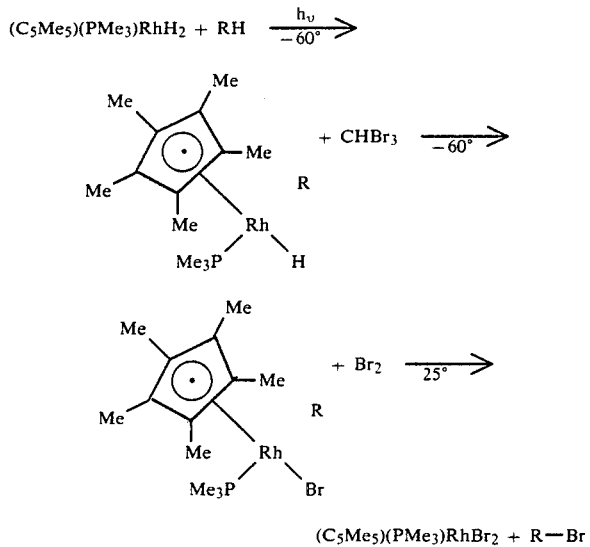

$(C_5Me_5)(PMe_3)RhBr_2$ + R—Br where:
($C_5Me_5$) represents a pentamethylated cyclopentadienyl radical, which is also represented herein at times by Cp,
($PMe_3$) represents a trimethylated phosphorous radical or a trimethylphosphine radical,
Rh represents a Rhodium atom,
H represents a hydrogen atom,
R represents an alkyl radical,
X represents a halogen atom as defined herein.

The R, as explained above, represents an alkyl radical and comes from the starting hydrocarbon used.

The reaction mechanism of this invention is generally applicable to all saturated hydrocarbons. However, preferred saturated hydrocarbons are those which have from about 2 to 20 hydrocarbons with the further provision that if they are not liquid when used alone, they are used in a mixture to be liquid at reaction conditions. More preferred are the saturated hydrocarbons of about 2-14 carbons which are liquid when used alone at reaction conditions (i.e., at a temperature in the range of about −60° to −20° C.). Included in the hydrocarbons discussed above are the acyclic and cyclic alkanes. The acyclic alkanes can be either of straight or branch-chained configuration. Acyclic hydrocarbons of about 2-12 carbons which are liquid at reaction conditions are the most preferred hydrocarbons. The cyclic compounds can have as few as 3 carbon atoms and up to about 8 carbon atoms in the ring. Preferred cyclic compounds are those of about 3 to 6 carbon atoms in the ring. The cyclic compounds can be substituted by either straight or branch-chained alkyl radical(s).

Specific illustrative examples of suitable hydrocarbons which can be used (i.e., alone or in a mixture to produce a liquid at reaction conditions) are:

| | |
|---|---|
| ethane | methyl cyclooctane |
| propane | propylcyclooctane |
| cyclopropane | n-nonane |
| isobutane | neooctane |
| n-pentane | n-decane |
| neopentane | cyclodecane |
| cyclopentane | 4-methyl decane |
| n-hexane | methyl cyclodecane |
| cyclohexane | n-dodecane |
| 2-methyl hexane | 2-propyl nonane |
| 3-methyl hexane | n-tetradecane |
| methyl cyclohexane | 2-methyl, 4-butyl decane |
| dimethyl cyclohexane | 6-hexyl dodecane |
| 2-ethyl hexane | 2-ethyl-hexylcyclodecane |
| 2,2′-dimethyl hexane | 1,4-dibutyl cyclooctane |
| 2-methyl, 4-ethyl hexane | n-eicosane |
| n-octane | |

The dihydridometal complex starting material in the process can be prepared in the manner taught by Isobe, Bailey and Maitlis, J. Chem. Soc., Dalton Trans. 1981, 2003 or Kang, Moseley, and Maitlis, J.A.C.S. 91, 5970 (1969). In brief, that process involves reacting a pentamethylated cyclopentadienyl rhodium dichloride dimer with trimethylphosphine and sodium bismethoxy ethoxy aluminum hydride to form the dihydridorhodium complex, (No. I) shown in the equation above. Other triorgano-phosphines (e.g. triphenylphosphine) can be used but trimethylphosphine is preferred. Also, other hydrides can be used, for example, lithium triethylborohydride.

The complex formed as above is then reacted in a series of reactions at mild conditions according to this invention to produce an alkyl halide and an organometal dihalide complex, (No. IV) above.

In the first step, the reaction of I and the alkane to be functionalized is carried out by subjecting the reactants to U.V. radiation (i.e. wavelength above about 210 nm) at a temperature of about −60° to −17° C. Preferred in most cases is a temperature in the range of about −35° to −20° C.

The above step can be carried out a superatmospheric or sub-atmospheric pressure, however atmospheric pressure is preferred because the results at the other pressures do not warrant the use of such extraordinary measures. Unless otherwise stated herein the same applies to all of the steps in this process.

One important consideration in connection with the above step is that dilution is desirable. To avoid many potential problems which include undesired side reactions, difficulties in separation of desired product, etc., a large excess of liquid hydrocarbon reactant is employed, where possible, instead of a separate solvent or diluent. Instead of stoichiometric, a dilution of about $1 \times 10^{-5}$ to $1 \times 10^{-2}$ molar concentration of the dihydride complex is beneficially employed. In the case of hydrocarbon reactants which are gaseous or solid (i.e., high molecular weight hydrocarbons) at reaction conditions, they require a solvent. Preferably, the solvent is inert or slow reacting so as to be practically inert at reaction conditions. However, in some cases, a lower molecular weight hydrocarbon desired to be functionalized can be conveniently used in lieu of a solvent as such.

In the next step, the complex formed in step (a) is reacted with a haloform of the formula $CHX_3$, where X represents a halogen atom. Although X can be bromine, iodine, or chlorine, bromine is preferred based on overall considerations. The reaction is carried out at a temperature in the range of about −60° to −17° C. Temperatures closer to ambient (i.e. by ambient is meant about 18°-20° C.) although still below ambient will be preferred to minimize the cost of cooling. With that and other factors in mind, a temperature in the range of about −35° to −20° C. will usually be preferred in this operation.

The preferred haloform, bromoform, can be conveniently added to the organo-metal complex by adding the neat liquid to a liquid bath or column of the complex to form halogenated product of the formula:

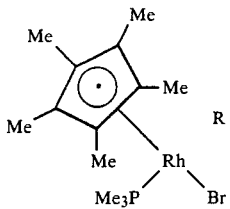

The halogenated organo-metal complex is next reacted with halogen (i.e. $Br_2$, a liquid at ambient; $I_2$, a solid at ambient; or $Cl_2$, a gas at ambient), preferably bromine, in the form of a liquid to generate the desired alkyl bromide product (or other halide corresponding to the reactants used). This reaction can be carried out by adding the bromine to the complex at about −60° to 25° C. (i.e. ambient) with ambient being preferred for obvious reasons of economics.

Also formed with the desired alkyl halide is a dihalo-counterpart of the starting organo-metal complex. This can be reused by regenerating through reaction of the by-product organo-metal complex with a known hydride source such as lithium aluminum hydride, lithium-triethylborohydride, sodium borohydride, sodium bis-methoxy ethoxy aluminum hydride (commercially available as Red-Al from Aldrich Chemical Company).

The following example is illustrative of the present invention, and is not to be regarded as limiting its scope.

EXAMPLE I

Experimental

All manipulations were carried out under $N_2$ unless otherwise noted. Hexane was distilled from n-butyllithium. $CHBr_3$ was deoxygenated by purging with $N_2$.

Preparation of $n_5$-$C_5Me_5RH$ $PMe_3$ $(C_2H_5)(B_u)$

A 20 ml cylindrical shaped pyrex "bomb" equipped with a teflon vacuum stopcock was changed with 50 mg of ($n_5$-$C_5Me_5$)$RhPMe_3H_2$(I). The system was evacuated, cooled to −190° C. and ~10 ml of ethane was added by vacuum transfer into the flask. The bomb was carefully warmed to −60° C. and the solution agitated until all of the dihydride was dissolved. The solution was then photolysed for 2 hours at −60° C. with a 200 watt Hanovia immersion Hg lamp. The solution was cooled to −190° C. and 35 μl of $CHBr_3$ added via syringe. The mixture was rewarmed to −60° C. and agitated for 5 minutes. The ethane was then removed in vacuo and the resulting residue extracted with hexane (5 × 10 ml). The undissolved material was dissolved in a minimum of $CH_2Cl_2$ and cooled to −40° C. to yield 18 mg of ($n_5$-$C_5Me_5$)$RhPMe_3Br_2$. The combined hexane extracts was filtered and concentrated under vacuum. The solution was cooled to −40° C. to yield 48 mg of ($n_5$-$C_5Me_5$)$RhPMe_3(C_2H_5)(Br)$.

Reaction of ($n_5$-$C_5Me_5$)$RhPMe_3(C_2H_5)(Br)$ with $Br_2$

A 10 ml flask equipped with a rubber septum and magnetic stirrer was changed with 20 mg of ($n_5$-$C_5Me_5$)$RhPMe_3(C_2H_5)(Br)$, 8 ml of hexane and 5 μl of $CHBr_3$ (as internal standard). The stirred solution was cooled to −78° C. and a mixture Bromine/hexane (11 mg $Br_2$ + 1 ml hexane) was added over a period of 10 minutes. The stirred solution was allowed to warm-up to room temperature and aliquot removed by syringe was analyzed by G C. From G. C. analysis, a calculated yield of bromoethane of approximately 80% based on ($n_5$-$C_5Me_5$)$RhPMe_3(C_2H_5)(Br)$.

The foregoing description of a preferred embodiment of the invention has been presented for purposes of illustration and description. It is not intended to be exhaustive, or to limit the invention to the precise form disclosed, and obviously many modifications and verifications are possible in light of the above teachings. The embodiment(s) was (were) chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A process for functionalizing saturated hydrocarbons comprising:

(a) reacting said saturated hydrocarbons of the formula:

RH where:
H represents a hydrogen atom, and
R represents a saturated hydrocarbon radical,
with a metal complex of the formula:

$CpRhPMe_3H_2$ where:
Cp represents a pentamethylated cyclopentadienyl radical,
Rh represents a rhodium atom,
P represents a phosphorous atom,
Me represents a methyl group,
H represents a hydrogen atom, in the presence of ultraviolet radiation at a temperature maintained at about −60° to −17° C. to form a hydridoalkyl complex of the formula:

$CpRhPMe_3(R)(H)$ (b) reacting said hydridoalkyl complex with a haloform of the formula:

$CHX_3$ where:
X represents a halogen atom selected from bromine, iodine and chlorine, at a temperature in the range of about $-60°$ to $-17°$ C. to form the corresponding haloalkyl complex of step (a) having the formula:

CpRhPMe$_3$(R)(X); and, (c) reacting said haloalkyl complex formed in (b) with halogen at a temperature in the range of about $-60°$ to $25°$ C. to form the alkyl halide of said saturated hydrocarbon.

2. A process according to claim 1 wherein the temperatures are in the ranges as follows:
(a) $-35°$ to $-20°$ C.
(b) $-35°$ to $-20°$ C.
(c) $0°$ to $20°$ C.

3. A process according to claim 1 wherein X is bromine.

4. A process according to claim 1 wherein the dilution of said metal complex in step (a) is in the range of about $1\times10^{-5}$ to $1\times10^{-2}$.

5. A process according to claim 1 wherein excess saturated hydrocarbon reactant is employed as solvent.

6. A process according to claim 1 wherein R is at least one hydrocarbon radical of up to about 20 carbon atoms whereby RH is a liquid at reaction conditions.

7. A process according to claim 1 wherein R is an acyclic hydrocarbon radical.

8. A process according to claim 7 wherein said saturated hydrocarbon reactant has about 2-12 carbon atoms.

9. A process according to claim 1 wherein R is a cyclic hydrocarbon radical.

10. A process according to claim 1 wherein R is a liquid hydrocarbon radical of up to about 14 carbon atoms.

11. A process for functionalizing saturated hydrocarbons comprising:
(a) reacting said saturated hydrocarbons of the formula:

R$_1$H where:
H represents a hydrogen atom, and
R$_1$ represents a saturated hydrocarbon radical, with a metal complex of the formula:

CpRhP(R$_2$)$_3$H$_2$ where:
Cp represents a pentamethylated cyclopentadienyl radical,
Rh represents a rhodium atom,
P represents a phosphorous atom,
R$_2$ represents a hydrocarbon radical,
H represents a hydrogen atom,
in the presence of ultraviolet radiation at a temperature maintained at about $-60°$ to $-17°$ C. to form a hydridoalkyl complex of the formula:

CpRhP(R$_2$)$_3$(R$_1$)(H)

(b) reacting said hydridoalkyl complex with a haloform of the formula:

CHX$_3$ where:
X represents a halogen atom selected from bromine, iodine and chlorine,
at a temperature in the range of about $-60°$ to $-17°$ C. to form the corresponding haloalkyl complex of step (a) having the formula:

CpRhP(R$_2$)$_3$(R$_1$)(X); and, (c) reacting said haloalkyl complex formed in (b) with halogen at a temperature in the range of about $-60°$ to $25°$ C. to form the alkyl halide of said saturated hydrocarbon.

* * * * *